United States Patent
Biehl

(10) Patent No.: US 9,201,009 B2
(45) Date of Patent: Dec. 1, 2015

(54) TEST METHOD FOR AN ESCAPE ROUTE MARKING

(75) Inventor: Torben Biehl, Hamburg (DE)

(73) Assignee: Lufthansa Technik AG, Hamburg (DE)

(*) Notice: Subject to any disclaimer, the term of this patent is extended or adjusted under 35 U.S.C. 154(b) by 200 days.

(21) Appl. No.: 13/983,016

(22) PCT Filed: Feb. 3, 2012

(86) PCT No.: PCT/EP2012/000484
§ 371 (c)(1),
(2), (4) Date: Oct. 14, 2013

(87) PCT Pub. No.: WO2012/104095
PCT Pub. Date: Aug. 9, 2012

(65) Prior Publication Data
US 2014/0291549 A1    Oct. 2, 2014

(30) Foreign Application Priority Data

Feb. 5, 2011   (DE) .......................... 10 2011 010 393

(51) Int. Cl.
| | |
|---|---|
| G01N 21/64 | (2006.01) |
| G01J 3/28 | (2006.01) |
| G01J 1/58 | (2006.01) |
| G01J 3/10 | (2006.01) |

(Continued)

(52) U.S. Cl.
CPC . *G01N 21/64* (2013.01); *G01J 3/28* (2013.01); *G01N 21/6408* (2013.01); *G01J 1/58* (2013.01); *G01J 3/10* (2013.01); *G01J 3/4406* (2013.01); *G01J 2001/4247* (2013.01); *G01N 2021/6417* (2013.01); *G01N 2021/6495* (2013.01)

(58) Field of Classification Search
CPC ........ G01J 3/28; G01N 21/64; G01N 21/6408
See application file for complete search history.

(56) References Cited

U.S. PATENT DOCUMENTS

| | | | |
|---|---|---|---|
| 6,307,207 B1* | 10/2001 | Burbank | 250/462.1 |
| 2003/0189823 A1* | 10/2003 | George et al. | 362/84 |

(Continued)

FOREIGN PATENT DOCUMENTS

| | | |
|---|---|---|
| DE | 10 2008 011 405 A1 | 9/2009 |
| DE | 10 2009 008 526 A1 | 8/2010 |

(Continued)

*Primary Examiner* — Christine Sung
(74) *Attorney, Agent, or Firm* — Vidas, Arrett & Steinkraus, P.A.; Scott Vidas

(57) ABSTRACT

A testing method for an escape path marking which has an installation position and is illuminated by a light source located in a defined position relative to the installation position, in order to charge the escape path marking for achieving afterglow,
the following steps:
An excitation curve A (λ) for the escape path marking is provided;
the irradiance E (λ) of the light source is recorded for the installation position of the escape path marking;
a weighted irradiance B (λ) is determined as a product of the irradiance and the excitation curve;
a charging irradiance (BiL) is determined as an integral over the weighted irradiance across the wavelength; and
a characteristic curve $K_{t1}$ (BiL) depending upon the charging time $t_1$ specifies what afterglow time emerges for the escape path marking with the charging time $t_1$ for the charging irradiance (BiL).

12 Claims, 2 Drawing Sheets

(51) Int. Cl.
*G01J 3/44* (2006.01)
*G01J 1/42* (2006.01)

(56) References Cited

U.S. PATENT DOCUMENTS

2006/0237689 A1* 10/2006 Fan et al. ............... 252/301.4 R
2007/0139643 A1   6/2007 Muraoka et al.
2008/0129996 A1   6/2008 Liu et al.
2009/0316147 A1  12/2009 Hamilton, II et al.
2010/0320371 A1* 12/2010 Agrawal et al. ................ 250/271
2012/0233895 A1*  9/2012 Martin et al. .................... 40/542

FOREIGN PATENT DOCUMENTS

WO   01/46615 A2   6/2001
WO   01/52224 A1   7/2001

* cited by examiner

TEST METHOD FOR AN ESCAPE ROUTE MARKING

STATEMENT REGARDING FEDERALLY SPONSORED RESEARCH

Not applicable.

CROSS-REFERENCE TO RELATED APPLICATIONS

This is a national stage application of PCT/EP2012/000484, filed on Feb. 3, 2012, which claims priority to DE 10 2011 010 393.7, filed on Feb. 5, 20911, the entire content of which are hereby incorporated by reference.

BACKGROUND OF THE INVENTION

The present invention relates to a test method for an escape path marking.

When utilising non-electric escape path markings, in particular if they are not charged by daylight, but by means of an artificial light source, it is to be ensured that the escape path marking possesses sufficient afterglow time. For use in aircraft, evidence needs to be provided that the escape path marking has sufficient afterglow time to be able to adequately light up the escape paths in the aircraft cabin in an emergency.

If an airline would like to install a non-electric escape path marking in an aircraft, first of all photometry is to be carried out at the installation position of the escape path marking, in order to verify that the lighting in the aircraft cabin is sufficiently bright to be able to adequately charge the escape path marking. The illumination level is measured with a conventional luxmeter. Irrespective of the wavelength, the luxmeter records the illumination level, which is given in lux (lx). Using this method, a defined light source with a defined spectral illumination level is utilised, in order to obtain convincing measurements. Depending upon the illumination level measured, a decision is then taken about whether the escape path marking generates sufficient afterglow time for the installation position.

Aircraft cabins are in future increasingly going to be lit by means of LED light systems. The use of LED light systems with different-coloured LEDs allows for a large number of different lighting scenarios (mixed colours) and light spectra. Depending upon the relative weighting of the radiant power of the light-emitting diodes, and depending upon the model of the light-emitting diodes, very different light spectra can be present here. In the case of lighting with LED light systems, it can therefore not be determined with the aid of a one-off measurement with the luxmeter whether lighting sufficient for the stipulated afterglow time occurs.

DE 10 2009 008 526 A1 discloses a method of ascertaining the luminous flux of optical rays, in particular light-emitting diodes. The luminous flux measurement is carried out separately, without fixed filter characteristics, in parallel, in accordance with the radiometric radiant power involved and the course of the optical spectrum of radiation of an emitter, using measuring devices, on a three-port integrating sphere, by means of a power-calibrated photodiode and an uncalibrated spectrometer. Their results, linked by switching, are damped based on a modifiable luminosity table, depending upon frequency, so that, in particular for monochromatically radiating LEDs, reproducible luminous flux results can be obtained in a cost-effective way.

BRIEF SUMMARY OF THE INVENTION

An object of the invention is to provide a testing method for an escape path marking, as well as a spectrometer for such, which allows for determining whether sufficient lighting is provided for an escape path marking, using a simple measurement.

The testing method according to the invention is provided for a photoluminescent escape path marking which can be arranged in an installation position and illuminated by a light source in a defined position relative to the installation position, in order to charge the escape path marking for achieving afterglow. In general, the irradiance of the light source is a decisive factor in regard to charging the photoluminescent escape path marking, so that, when examining the escape path marking, it is always to be taken into consideration in which positions relative to one another the light source and the escape path marking are to be found. In the case of the method according to the invention, as a first procedural step an excitation curve A ($\lambda$) is provided for the escape path marking, depending upon the wavelength. The latter can be measured, or, based on technical data on a photoluminescent material, be ascertained in the escape path marking. The excitation curve specifies, for example, the relative spectral weight with which an escape path marking is charged. As a further procedural step, the irradiance E ($\lambda$) of the light source is recorded for the installation position of the escape path marking, depending upon the wavelength. The irradiance is determined in the known SI units, for example as W/m$^2$ as the irradiance of the light source for the escape path marking, depending upon the wavelength. The irradiance E ($\lambda$) for the installation position may be determined at the site of the escape path marking or also separately prior to installing the escape path marking.

In a further procedural step of the testing procedure according to the invention, a weighted irradiance is ascertained, depending upon the wavelength. The weighted irradiance emerges as the product of the irradiance and the excitation curve, depending upon the wavelength. The weighted irradiance is a measure of what contribution to the excitation the irradiance supplies per wavelength. In a further procedural step of the method according to the invention, a charging irradiance (BiL) is ascertained as an integral over the weighted irradiance. Instead of an integral, a corresponding sum of the values is also possible. The charging irradiance (BiL) is a measure of to what extent the escape path marking is charged.

As a subsequent step, depending upon the charging time $t_1$, it is ascertained with the aid of a characteristic curve $K_{t1}$ (BiL) what afterglow time transpires for the escape path marking with the charging time $t_1$. The characteristic curve $K_{t1}$ (BiL) is determined empirically, and provided for the testing procedure. Should several different values be contemplated for the afterglow time, a set of characteristic curves $K_{t1}$ (BiL) can also be used, which has a respective characteristic curve $K_{t1}$ (BiL) for a value $t_1$. Other than in the case of the known methods, with the method in accordance with the invention both the excitation curve of the escape path marking and the irradiance are taken into account, depending upon the wavelength. An LED light system with its specific spectral radiation leads to a specific irradiance, so that a specific value for the charging irradiance emerges from the latter. Since the method according to the invention focuses on the charging irradiance, the latter is independent of the light system used and the latter's spectral radiation. Prior to specifically utilising the escape path marking, it is only necessary to ascertain the charging irradiance, in order to obtain a reliable statement on the afterglow time to be expected with a specified charging time.

In a preferred embodiment, changes in the spectrum through colour filters may also be taken into consideration separately. With escape path markings, it is possible to achieve further colours different from a primary colour of the photoluminescent material, such as yellow-green, by using colour filters. Such colour filters are, for example, laid on top of the photoluminescent material as a layer or film. The colour filters reduce the light coming from the light source, falling upon the photoluminescent material, wherein spectral transmission behaviour is assigned to each colour filter. When using colour filters for the photoluminescent material, it is therefore advantageous to take the transmission behaviour of the colour filter into account in regard to the irradiance. This is done in such a way as if the light source was equipped with the colour filter. The irradiance E ($\lambda$) of the light source would be multiplied by the spectral transmission behaviour T ($\lambda$), in order to determine the effective efficient irradiance of the light source for the photoluminescent material.

In a preferred embodiment, the characteristic curve $K_{t1}$ (BiL) is determined by measuring the associated afterglow time for multiple charging irradiances and using it as a respective support point of the characteristic curve. In the testing procedure provided, an empirically ascertained characteristic curve is used. The characteristic curve is determined by interpolation and/or extrapolation, based on support points.

In a preferred further development of the testing procedure, a set of characteristic curves $K_{t1}$ (BiL) is ascertained for multiple charging times. In this way, with a pre-determined charging irradiance (BiL) a reliable statement can be made on what minimum charging period is necessary to achieve a desired or required afterglow time.

In a preferred embodiment of the testing procedure, light-emitting diodes, which can be set in their luminosity to determine the characteristic curve, are provided as light sources, so as to achieve various different charging irradiances. In this way, the characteristic curve provided for the testing procedure can be ascertained without great technical effort by setting the charging irradiances.

In a preferred embodiment of the testing method according to the invention, an excitation curve $A_{pig}$ ($\lambda$) of the luminescent pigments in the escape path marking is used as the excitation curve A ($\lambda$) for an escape path marking. The advantage of this embodiment of the testing method lies in the fact that the excitation curve of the luminescent pigments utilised in the escape path marking is well known and measuring it can therefore be dispensed with.

In the case of the testing method according to the invention, the irradiance E ($\lambda$) is preferably measured using a spectrometer.

In an expedient embodiment of the testing method, the irradiance E ($\lambda$) is determined for a mean distance between the light source and the escape path marking. Focusing on a mean distance permits complex geometries between the installation position of the escape path marking and the positions of the light sources to be taken into account, in order to determine a reliable irradiance. The mean distance is determined from the distances existing in the actual geometry, by means of averaging. In particular when recording the characteristic curve, it proves to be particularly advantageous to aim at a mean distance between the light source and the escape path marking.

According to the invention, the object is likewise solved through a spectrometer for testing an escape path marking. The escape path marking is illuminated in an installation position relative to a light source, by the latter, in order to charge the escape path marking for achieving afterglow. The spectrometer according to the invention has a memory for accumulating an excitation curve A ($\lambda$) for the escape path marking, depending upon the wavelength. The spectrometer further includes a spectral measuring device, which records the irradiance of the light source for the installation position of the escape path marking, depending upon the wavelength. In addition, a further memory is provided for accumulating a particular irradiance B ($\lambda$). Means for multiplying the irradiance and the excitation curve are likewise provided. An integration means accesses the further memory to integrate the accumulated irradiance over the wavelength range and thus determine a charging irradiance (BiL). Moreover, an evaluation means having a set of characteristic curves $K_{t1}$ (BiL) depending upon the charging time $t_1$ is provided, wherein one of the characteristic curves $K_{t1}$ (BiL) specifies an afterglow time for the escape path marking with the charging time $t_1$ for the charging irradiance (BiL) ascertained by the integration means. The spectrometer according to the invention permits a reliable statement to be made on whether an escape path marking provided possesses a sufficient afterglow time for a charging time. A suitable photometer may also be provided for as an evaluation means of the spectrometer according to the invention.

Advantageously, the spectrometer is also provided with means of multiplying the irradiance E ($\lambda$) by a transmission spectrum T ($\lambda$) of a colour filter of the escape path marking. The means of multiplication allows for also taking into account escape path markings in the case of which the charging and radiation of the photoluminescent material occur through colour filters.

The invention further comprises a computer for implementing the testing procedure according to the invention, wherein the computer has a data input in order to read the excitation curve A ($\lambda$), the illumination level B ($\lambda$), the charging time $t_1$ and a set of characteristic curves $K_{t1}$ (BiL) and a data output for the resulting afterglow time. The afterglow time is calculated on the computer, according to the testing procedure according to the invention.

In a preferred embodiment, a computer is provided in order to also take into account a transmission spectrum T ($\lambda$) of the colour filter of the escape path marking.

The testing procedure according to the invention is explained in further detail based on an embodiment. In the figures:

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
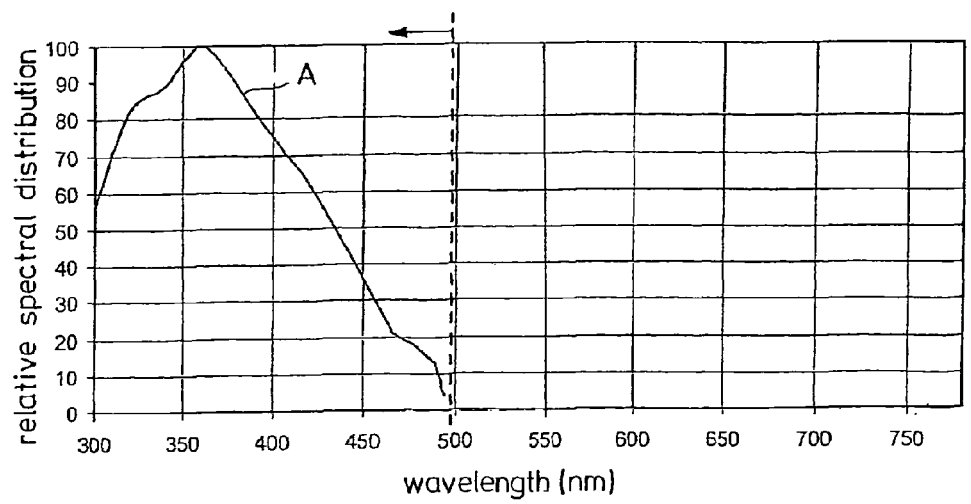
FIG. 1 shows an excitation curve A ($\lambda$) for an escape path marking.

FIG. 1 shows an excitation curve A ($\lambda$) for an escape path marking. The excitation curve A ($\lambda$) is shown as a relative excitation over the wavelength of the excitatory light. The excitation curve is standardised to 100% in FIG. 1. The maximum excitation of the escape path marking occurs for a wavelength of approx. 360 nm. In a wavelength range above 500 nm, no excitation of the pigments takes place. As a preferred escape path marking, pigments based on strontium aluminate ($SrAl_2O_4$) are used. It is also usual to utilise pigments on the basis of ZnS. Usually, the pigments used for the escape path marking radiate in a wave band above 500 nm, for example 510 nm to 540 nm. The photoluminescent pigments are, however, excited in a lower wavelength range, for example from 200 nm to 450 nm.

Figure 2:
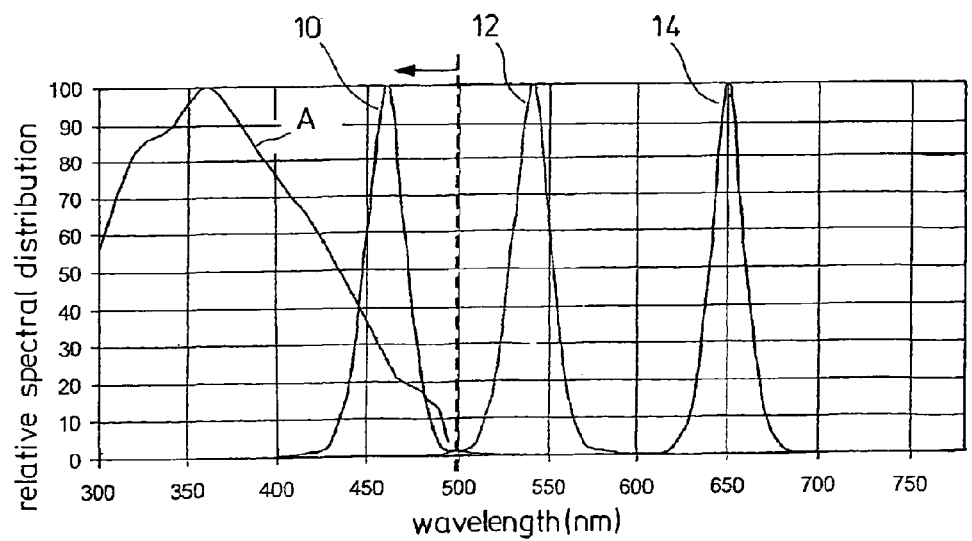
FIG. 2 shows the excitation curve from FIG. 1 together with an emission spectrum of an LED lighting system.

FIG. 2 shows the emission spectrum of the LED lighting system. In order to generate white light, green, blue and red light-emitting diodes are mixed with one another. Each of the light-emitting diodes has an emission spectrum of 10, 12 and 14. In FIG. 2, the emission spectra of the light-emitting diodes are likewise standardised to the value of 100%, for a better overview. This is, however, not at all necessary; it is indeed possible for the light-emitting diodes to have different illumination levels in relation to one another.

It becomes clear from the representation in FIG. 2 that only the blue light-emitting diodes with their emission spectrum 10 contribute towards exciting the pigments with the excitation curve A. The light emitted by the green and red light-emitting diodes does not contribute towards charging the escape path marking. It also becomes clear from the latter why an overall measurement of the irradiance is undertaken with a spectrometer, and a luxmeter alone is not sufficient to undertake a reliable examination of the escape path marking. In the case of a measurement with a luxmeter, the contribution of the green and the red light-emitting diodes is likewise measured, although it does not contribute towards exciting the escape path marking. For a better conceptual differentiation, in the case of the invention it is the irradiance which is focused on, which in radiometry corresponds to the concept of the illumination level from photometry.

Figure 3:
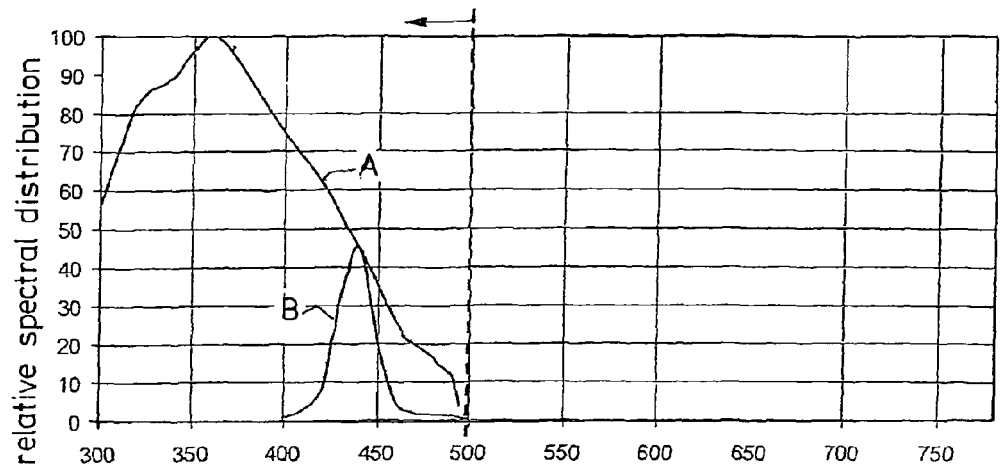
FIG. 3 shows the weighted spectrum of the LED lighting system from FIG. 2.

FIG. 3 shows a weighted illumination level B, which emerges from the weighting of the emission spectrum 10 with the curve A in FIG. 2. The weighted emission spectrum B is, in turn, a function of the wavelength. It can clearly be discerned in FIG. 3 that the maximum of the emission spectrum 10 is to be found in its unweighted state above 450 nm, whereas the weighted emission spectrum reaches its maximum at a value of below 450 nm. Due to the flank of the excitation curve A declining sharply between 360 nm and 500 nm, the maximum of the weighted emission spectrum is shifted.

For a simpler representation in the figures, the emission spectra shown in FIGS. 2 and 3 and the weighted emission spectrum B' involve any further units desired.

In the case of the testing procedure according to the invention, it is not the emission spectrum of the light-emitting diodes that is focused on, but a recorded irradiance $E(\lambda)$. The dependence of the irradiance upon the positions of the escape path marking in relation to the light source emerges from the fact that the irradiance decreases with the distance, so that, at a greater distance, one and the same light source has a weaker irradiance. In the case of the method according to the invention, it is then not the spectral emission spectrum, as shown in the figures, that is determined, but the weighted irradiance. Qualitatively, however, depending upon the wavelength, both the irradiance and the weighted irradiance show the same spectral course as the emission spectra, only with the difference that the weighted irradiance specifies the irradiance in $W/m^2$ for a wavelength.

In the case of the method according to the invention, the corresponding values are added up or integrated across or over the weighted irradiance $B(\lambda)$, in order to determine the charging irradiance (BiL). In regard to FIG. 3, this means that the surface underneath the curve B' is determined The surface is a measurement of how intensively, in total, the escape path marking is excited by the lighting system.

Figure 4:
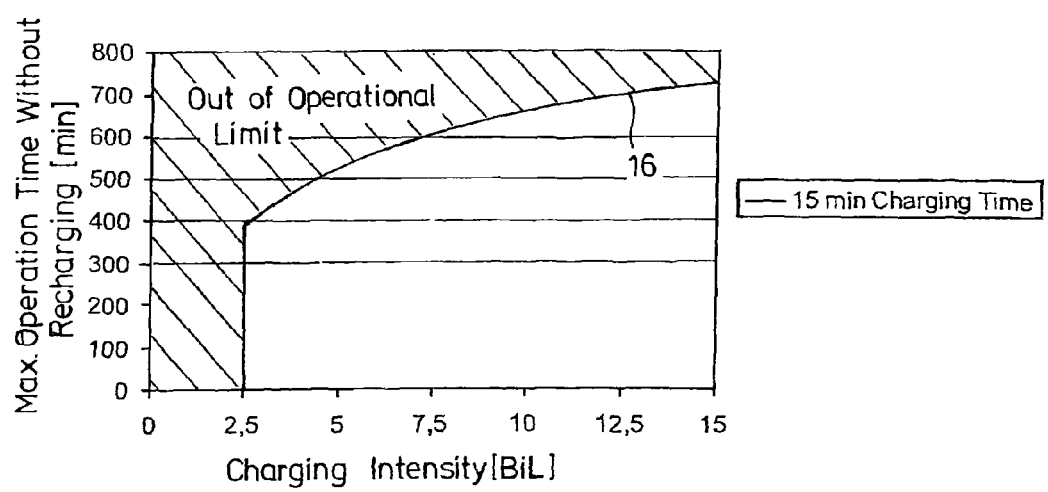
FIG. 4 shows the characteristic curve with a charging time of 15 minutes, depending upon the charging irradiance.

FIG. 4 shows a characteristic curve 16, which specifies, for a charging time of 15 minutes, at which charging irradiance (BiL) which maximum afterglow time emerges for the escape path marking. It can be inferred from the curve that, for a maximum afterglow time of 400 minutes, a charging irradiance of at least 2.5 is required. At a charging irradiance of 7.5, an afterglow time of 600 minutes emerges.

The method according to the invention allows for determining the charging irradiance for a specific light system and a specific installation position of the escape path marking relative to the light system. Based on the characteristic curve, it can then be ascertained whether a sufficient afterglow time is achieved for such a charging irradiance. Should the testing method be determined for multiple different charging times, an independent characteristic curve 16 is to be obtained for each charging time. Measurements have shown that the set of characteristic curves resulting in this way runs essentially parallel.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A testing method for an escape path marking which has an installation position and is illuminated by a light source in a defined position relative to the installation position, in order to charge the escape path marking for achieving afterglow, the method comprising the following steps:

An excitation curve $A(\lambda)$ for the escape path marking is provided, depending upon a wavelength;

an irradiance $E(\lambda)$ of the light source is recorded for the installation position of the escape path marking, depending upon the wavelength;

a weighted irradiance $B(\lambda)$ is determined as a product of the irradiance and the excitation curve, depending upon the wavelength;

a charging irradiance (BiL) is determined as an integral over the weighted irradiance across the wavelength; and a characteristic curve $K_{t1}$ (BiL) depending upon the charging time $t_1$ specifies what afterglow time emerges for the escape path marking with a charging time $t_1$ for the charging irradiance (BiL).

2. The testing method according to claim 1, wherein the irradiance $E(\lambda)$ of the light source is multiplied by a transmission spectrum $T(\lambda)$ of a colour filter of the escape path marking.

3. The testing method according to claim 1, wherein the characteristic curve $K_{t1}$ (BiL) is ascertained by measuring the associated afterglow time for multiple charging irradiances (BiL) and respectively using it as a support point of the characteristic curve.

4. The testing method according to claim 3, wherein a set of characteristic curves $K_{t1}$ (BiL) is ascertained for multiple charging times.

5. The testing method in accordance with claim 3, wherein the light source is light-emitting diodes, the irradiance of which can be set to determine the characteristic curve in order to achieve different charging irradiances.

6. The testing method according to claim 1, wherein an excitation curve $A_{pig}(\lambda)$ of the luminescent pigments in the escape path marking is used as the excitation curve $A(\lambda)$ for the escape path marking.

7. The testing method according to claim 1, wherein the irradiance $E(\lambda)$ is measured with a spectrometer.

8. The testing method according to claim 7, wherein the irradiance E (λ) is determined for a mean distance between the light source and the escape path marking.

9. The testing method of claim 1 further providing a computer, wherein the computer has a data input, in order to read the excitation curve A (λ), the weighted irradience B (λ), the charging time $t_1$ and a set of characteristic curves $K_{t1}$ (BiL), and a data output for the afterglow time resulting.

10. The testing method of claim 9, wherein the data input is configured to read a transmission spectrum T (λ) of a color filter of the escape path marking.

11. A spectrometer for testing an escape path marking which has an installation position and is illuminated by a light source located in a defined position relative to the installation position, in order to charge the escape path marking for achieving afterglow, wherein the spectrometer comprises:

a memory for accumulating an excitation curve A (λ) for the escape path marking, depending upon a wavelength;

a spectral measuring device, which records irradiance of the light source for the installation position of the escape path marking, depending upon the wavelength; a further memory for accumulating a weighted irradiance B (λ), as well as a means of multiplying the irradiance and the excitation curve; integration means, which access the further memory to integrate the accumulated irradiance over the wavelength and thus determine a charging irradiance (BiL); and evaluation means having a set of characteristic curves $K_{t1}$ (BiL) depending upon a charging time $t_1$, wherein one of the characteristic curves $K_{t1}$ (BiL) specifies an afterglow time for the escape path marking with the charging time $t_1$ for the charging irradiance (BiL) ascertained by the integration means.

12. The spectrometer according to claim 11, wherein further means of multiplying the irradiance of the light source E (λ) by a transmission spectrum T(λ) of a colour filter of the escape path marking are provided.

\* \* \* \* \*